(12) United States Patent
Mihajlovic et al.

(10) Patent No.: US 10,481,864 B2
(45) Date of Patent: Nov. 19, 2019

(54) METHOD AND SYSTEM FOR EMOTION-TRIGGERED CAPTURING OF AUDIO AND/OR IMAGE DATA

(71) Applicant: Stichting IMEC Nederland, Eindhoven (NL)

(72) Inventors: Vojkan Mihajlovic, Eindhoven (NL); Stefano Stanzione, Veldhoven (NL); Ulf Grossekathoefer, Eindhoven (NL)

(73) Assignee: Stichting IMEC Nederland, Eindhoven (NL)

( * ) Notice: Subject to any disclaimer, the term of this patent is extended or adjusted under 35 U.S.C. 154(b) by 114 days.

(21) Appl. No.: 15/717,854

(22) Filed: Sep. 27, 2017

(65) Prior Publication Data

US 2018/0088903 A1 Mar. 29, 2018

(30) Foreign Application Priority Data

Sep. 28, 2016 (EP) .................................... 16191059

(51) Int. Cl.
*G10L 25/00* (2013.01)
*G06F 3/16* (2006.01)
(Continued)

(52) U.S. Cl.
CPC ............ *G06F 3/167* (2013.01); *A61B 5/0476* (2013.01); *A61B 5/0488* (2013.01);
(Continued)

(58) Field of Classification Search
CPC . G06F 3/16; G10L 25/63; G10L 25/18; G10L 25/90; G10L 15/22; G10L 15/265;
(Continued)

(56) References Cited

U.S. PATENT DOCUMENTS

| 2002/0171551 A1* | 11/2002 | Eshelman ............... G06Q 50/22 340/573.1 |
| 2009/0023422 A1 | 1/2009 | Macinnis et al. |

(Continued)

FOREIGN PATENT DOCUMENTS

| EP | 2 376 207 B1 | 8/2015 |
| GB | 2 398 423 A | 8/2004 |

(Continued)

OTHER PUBLICATIONS

European Search Report, European Patent Application No. 16191059. 1, dated Apr. 11, 2017, 8 pages.
(Continued)

*Primary Examiner* — Edgar X Guerra-Erazo
(74) *Attorney, Agent, or Firm* — McDonnell Boehnen Hulbert & Berghoff LLP

(57) ABSTRACT

The present disclosure relates to a method for emotion-triggered capturing of audio and/or image data by an audio and/or image capturing device. The method includes receiving and analyzing a time-sequential set of data including first physiological data representing a first physiological parameter corresponding to a first person, a second physiological data representing a second physiological parameter corresponding to a second person, and voice audio data including a voice of at least one of the first and the second person, to determine whether a simultaneous change of emotional state of a first person and a second person occurs and transmitting a trigger signal to the capturing device. The present disclosure also relates to a corresponding apparatus and a system comprising the apparatus.

20 Claims, 3 Drawing Sheets

(51) Int. Cl.
| | |
|---|---|
| G10L 25/18 | (2013.01) |
| G10L 25/63 | (2013.01) |
| G10L 25/90 | (2013.01) |
| H04N 5/232 | (2006.01) |
| A61B 5/00 | (2006.01) |
| A61B 5/0476 | (2006.01) |
| A61B 5/0488 | (2006.01) |
| A61B 5/053 | (2006.01) |
| A61B 5/16 | (2006.01) |
| H04N 5/77 | (2006.01) |

(52) U.S. Cl.
CPC ............ *A61B 5/0533* (2013.01); *A61B 5/165* (2013.01); *A61B 5/7285* (2013.01); *G10L 25/18* (2013.01); *G10L 25/63* (2013.01); *G10L 25/90* (2013.01); *H04N 5/232* (2013.01); *H04N 5/23203* (2013.01); *H04N 5/77* (2013.01); *A61B 2560/029* (2013.01)

(58) Field of Classification Search
CPC ............ G10L 17/005; G10L 2015/227; G06K 9/00335
See application file for complete search history.

(56) References Cited

U.S. PATENT DOCUMENTS

| | | | |
|---|---|---|---|
| 2012/0293773 A1* | 11/2012 | Publicover | A61B 3/113 351/210 |
| 2013/0054090 A1 | 2/2013 | Shin et al. | |
| 2014/0234815 A1 | 8/2014 | Jang et al. | |
| 2015/0193507 A1* | 7/2015 | Rappoport | G06Q 10/101 382/118 |
| 2016/0070245 A1 | 3/2016 | Lee et al. | |
| 2018/0075490 A1* | 3/2018 | Chintalapoodi | G06K 9/00302 |

FOREIGN PATENT DOCUMENTS

| | | |
|---|---|---|
| WO | 2007/034442 A2 | 3/2007 |
| WO | 2007/034442 A3 | 3/2007 |
| WO | 2015/019345 A1 | 2/2015 |

OTHER PUBLICATIONS

Kim, Jonghwa, "Bimodal Emotion Recognition Using Speech and Physiological Changes", Robust Speech Recognition and Understanding, Chapter 15, Edited by Michael Grimm and Kristian Kroschel, Published by the I-Tech Education and Publishing, Vienna, Austria, Jun. 2007, pp. 265-280.

Liu, Yisi et al., "Real-Time EEG-Based Emotion Recognition and Its Applications", Transactions on Computational Science XII, LNCS, vol. 6670, 2011, pp. 256-277.

Ramakrishnan, S., "Recognition of Emotion From Speech: A Review", Chapter 7, Speech Enhancement, Modeling and Recognition-Algorithms, and Applications, Published by InTech, Mar. 14, 2012, pp. 121-138.

Truong, K, Van Leeuwen, D.: An open-set Detection Evaluation Methodology for Automatic Emotion Recognition in Speech. In: Workshop on Paralinguistic Speech—between models and data, pp. 5-10 (2007).

Schut, Marleen H. et al., "Biometrics for Emotion Detection (BED): Exploring the Combination of Speech and ECG", Proceedings of the 1st International Workshop on Bio-Inspired Human-Machine Interfaces and Healthcare Applications, Jan. 21, 2010, pp. 8 pages.

\* cited by examiner

METHOD AND SYSTEM FOR EMOTION-TRIGGERED CAPTURING OF AUDIO AND/OR IMAGE DATA

CROSS-REFERENCE TO RELATED APPLICATIONS

The present application is a non-provisional patent application claiming priority to European Patent Application No. 16191059.1, filed Sep. 28, 2016, the contents of which are hereby incorporated by reference.

FIELD OF THE DISCLOSURE

The present disclosure relates to a method and a system for controlling capturing of audio and/or image data based on emotional state in a scene.

BACKGROUND

Today, recording of scenes is very common. Audio and/or image data, such as still images and videos, are captured in many different situations. For instance, people want to record significant events in order to be able to later share the events with others and to create memories from the events. Hence, when a significant event occurs, people use smart phones or other audio or image/data capturing devices to immediately record the event.

Further, it is increasingly common that audio and/or image capturing devices are permanently installed in certain locations. For instance, conferencing equipment may be installed in conference rooms and surveillance systems may be installed in people's homes.

An amount of audio and/or image data recorded by capturing devices is already enormous and hard to manage. Thus, it would be desired that audio and/or image data is only captured when actually relevant. This capture of relevant data is commonly used in surveillance systems, when images and/or videos are only captured once an alarm event occurs.

It would be desired to improve control of audio and/or image data capturing devices in relation to a relevance of a scene to people.

US 2014/0234815 discloses an emotion signal detecting apparatus including a sensor unit which detects a biological signal and an environmental signal of a user, and a control unit configured to generate emotion information based on the biological signal and the environmental signal.

However, there is need for improvement in using an emotional state for controlling capture of a scene.

SUMMARY

Certain objects of the present disclosure may provide automatic capturing of moments/events which are of great value to people.

This and other objects of the disclosure may be at least partly met by the disclosure as defined in the independent claims. Example embodiments are set out in the dependent claims.

In a first aspect, the present disclosure relates to a method for emotion-triggered capturing of audio and/or image data by an audio and/or image capturing device. The method comprises: receiving a time-sequential set of data including first physiological data representing a first physiological parameter corresponding to a first person, a second physiological data representing a second physiological parameter corresponding to a second person, and voice audio data including a voice of at least one of the first and the second person; analyzing the time-sequential set of data to determine whether a set of one or more features obtainable from the set of data matches a set of one or more predetermined characteristics being indicative of a simultaneous change of emotional state of the first person and the second person; and in response to determining that the set of one or more features matches the set of one or more predetermined characteristics, transmitting a trigger signal to the capturing device.

An emotional state of a first and a second person may be determined based on the first physiological data, the second physiological data and the voice audio data. This implies that a change of emotional state of the first person and the second person may be identified.

According to example embodiments of the disclosure, a simultaneous change of emotional state of a first person and a second person is used to control automatic capturing of audio and/or image data. For instance, the simultaneous change of emotional state of parents when their baby starts walking, or another significant event occurs, may be used to trigger capturing of audio and/or image data such that the moment can be perpetuated.

According to example embodiments of the disclosure, the emotional state of a social group which is present in a scene may be used for triggering capture of audio and/or image data. The emotional state of the group is used by means of the simultaneous change of emotional state of at least two persons. However, if there is a large social group present in the scene, more than two persons may need to simultaneously change emotional state in order for a trigger signal to be transmitted or outputted.

An emotional predominance in the scene may be estimated. Such emotional predominance may be derived from physiological data and voice audio data for all, or most persons involved in a social interaction in the scene. A change of emotional predominance in the scene based on simultaneous change of an emotional state of a plurality of persons may thus be used for emotion-triggered capturing of audio and/or image data.

The simultaneous change in emotional state may have both positive and negative valence (and high arousal). Thus, if a heated discussion takes place, this may also cause capturing of audio and/or image data.

The social group in which at least the first and second persons are included may range from family members within their home to co-workers in a meeting room and to audience attending a social event (for example, a concert or a theater show).

The first and second persons may be physically present in the same scene, but they could also be meeting in a virtual setting, such as a remote videoconference meeting.

The audio and/or image capturing device may be a simple video camera or a microphone, or may be a complex system that includes a large number of sensors (video cameras, digital cameras, microphones, etc.). The audio and/or image capturing device may be pre-installed in a scene such that the triggering of capturing of audio and/or image data makes use of equipment which is anyway installed in the scene (such as videoconferencing system in a conference room or surveillance systems in a home).

The physiological data may be captured using sensors which may be worn by the first and second persons. For instance, use may be made of smart phones or wearables, which anyway may be worn by the persons and which may capture physiological data, which together with voice audio data may be used for determining an emotional state of the first and second persons.

Audio and/or image data may be triggered when an emotional predominance in the scene indicates that the event or moment is of importance. Hence, in example embodiments, the disclosure allows capturing audio and/or image data of important events/moments, without requiring capturing of lengthy sequences of audio and/or image data. Thus, in example embodiments, the disclosure allows saving storage memory in that only relevant audio and/or image data may be captured. Also, in example embodiments, the disclosure allows saving power as the audio and/or image data capturing device need only be activated when necessary.

According to an example embodiment, the analyzing comprises: determining whether a set of features based on the first physiological data, the second physiological data, and the voice audio data in combination corresponds to a set of characteristics indicative of a change of emotional state of both the first person and the second person. Thus, a set of predetermined characteristics may be based on a combination of physiological data for both the first and second person and on voice audio data including a voice of at least one of the first and the second person. The analyzing may thus determine when the time-sequential set of data, as a whole, indicates a simultaneous change of emotional state of both the first and the second person.

According to an example embodiment, the analyzing comprises: identifying that the first physiological data and the voice audio data represents a first change of emotional state of the first person at a first point of time in the time-sequential set of data; identifying that the second physiological data and the voice audio data represents a second change of emotional state of the second person at a second point of time in the time-sequential set of data; determining whether a simultaneous change of emotional state occurred based on a difference between the first and second points of time. Thus, a separate detection of a change of emotional state may be performed for the first person and the second person. A time difference between the change of emotional state of the first person and the change of emotional state of the second person may be used to determine whether the changes of emotional state occurred simultaneously. If the emotional states of the first and second persons change within a time difference less than a set threshold, it could be concluded that a simultaneous change of emotional states has occurred and that the change of emotional state may be due to an event occurring in the scene. Thus, the audio and/or image capturing device may be triggered in order to capture the event.

The voice audio data may be analyzed to filter out voice audio data belonging to the first and second persons, respectively, for example, based on pitch, entropy and tempo. Thus, data representative of the respective persons may be used separately for determining the emotional states of the respective persons.

Also, the first and second persons need not be at the same location, for example, if the first and the second person interact through a videoconference. In such case, separate voice audio data may be captured for the first and the second person, such that there may be no need of filtering in order to determine the voice audio data corresponding to the respective persons.

The analyzing of the time-sequential data may include both analyzing a combination of data of the first and the second person to determine whether a simultaneous change of emotional state has occurred and separately analyzing data of the respective persons to determine changes of emotional states of the respective persons. Results of such analyses may then be combined to decide whether a simultaneous change of emotional state has occurred.

According to an example embodiment, the set of one or more features comprise low-level features, which may be directly extracted from the time-sequential set of data, and high-level concepts, which may be derived by applying data analysis on the time-sequential set of data.

High-level concepts may be formed based on expert-provided input or previously determined knowledge on how a transition from one emotional state to another can be described in terms of concurrent change of a set of low-level features or signals. Such information may be part of a database, such that the data analysis may comprise analyzing the time-sequential set of data to information in the database. However, the determination of high-level concepts may also be used for forming an algorithm that may be used to extract the high-level concept based on a (sub)set of low-level features. Hence, the data analysis may include applying an algorithm to the time-sequential set of data to determine whether the high-level concept is met.

According to an embodiment, the set of one or more predetermined characteristics include group profiles, which define a combination of a plurality of predetermined characteristics in relation to the first and the second person, which plurality of predetermined characteristics are correlated with respect to a simultaneous change of emotional state of the first person and the second person. The group profiles may thus provide information allowing parallel processing of the time-sequential data of the first and the second persons to determine whether a simultaneous change of emotional state of the first and the second person occurs.

According to an example embodiment, the features include one or more of: a variation of the first physiological parameter, a variation of the second physiological parameter, a maximum value of the first physiological parameter, a maximum value of second physiological parameter, a mean value of the first physiological parameter, a mean value of the second physiological parameter, a standard deviation of the first physiological parameter, a standard deviation of the second physiological parameter, a correlation of the first physiological parameter, a correlation of the second physiological parameter, a coherence of the first physiological parameter, a coherence of the second physiological parameter, an increase of the first physiological parameter, an increase of the second physiological parameter, a decrease of the first physiological parameter, a decrease of the second physiological parameter, a cease of the first physiological parameter, and a cease of the second physiological parameter.

The first and the second physiological parameter may relate to the same type of physiological measurement, albeit for the first and the second person, respectively. Alternatively, the first and the second physiological parameter may relate to different types of physiological measurements.

A plurality of the features may be used to form a set of features which may be matched to a set of predetermined characteristics in order to determine a simultaneous change of emotional state of the first and the second person.

According to an example embodiment, the features include one or more of: an amplitude of the voice audio data, a variation of an amplitude of the voice audio data, an increase of an amplitude of the voice audio data, a decrease of an amplitude of the voice audio data, a pitch of the voice audio data, a variation of a pitch of the voice audio data, mel-frequency spectral coefficients of the voice audio data, a variation of mel-frequency spectral coefficients of the voice audio data, linear prediction spectral coefficients of the voice audio data, a variation of linear prediction spectral coefficients of the voice audio data, a time separation between consecutive sounds of the voice audio data, a variation of a time separation between consecutive sounds of the voice audio data, an increase of a time separation between consecutive sounds of the voice audio data, a decrease of a time separation between consecutive sounds of the voice audio data, a background noise level of the voice audio data, a variation of a background noise level of the voice audio data, an increase of a background noise level of the voice audio data, a decrease of a background noise level of the voice audio data, a predominant frequency of the voice audio data, a variation of a predominant frequency of the voice audio data, an increase of a predominant frequency of the voice audio data, and a decrease of a predominant frequency of the voice audio data.

The features may thus provide information relating to audio data which may be used for determining a change of emotional state of a person. A tone of the voice of a person may be changed when the emotional state changes, which may be detected using one or more of the above features.

According to an example embodiment, the first physiological parameter and the second physiological parameter include one or more of: galvanic skin response, electroencephalogram, photoplethysmogram, bio-impedance, electromyogram, electrooculogram and electrocardiogram. These physiological parameters may provide information of the emotional state of a person, which may be used in combination with voice audio data to determine a change of the emotional state of a person.

Using a plurality of types of physiological parameters may allow determining a change of emotional state with a high degree of certainty as multiple indicators of the change of emotional state may be analyzed.

The features may include one or more of: information extractable from galvanic skin response, electroencephalogram, photoplethysmogram, bio-impedance, electromyogram, electrooculogram or electrocardiogram measurements. Thus, the features may be based on any type of information that may be extracted from these types of measurements.

According to an example embodiment, the determining of whether the set of one or more features obtainable from the set of data matches a set of one or more predetermined characteristics includes one or more of: determining whether one or more of the features exceeds a predetermined set of thresholds, determining whether one or more of the features fall below a predetermined set of thresholds, and determining whether one or more of the features corresponds to a predetermined set of characteristics. The set of one or more features may be considered to match the set of one or more predetermined features if a predetermined number of features meet the required relation to the set of thresholds or characteristics.

In a second aspect, the present disclosure relates to an apparatus for emotion-triggered control of capture of audio and/or image data by an audio and/or image capturing device. The apparatus comprises: data input circuitry adapted to: receive a time-sequential set of data including first physiological data representing a first physiological parameter corresponding to a first person, a second physiological data representing a second physiological parameter corresponding to a second person, and voice audio data including a voice of at least one of the first and the second person, and a processing unit adapted to: analyze the time-sequential set of data to determine whether a set of one or more features obtainable from the set of data matches a set of one or more predetermined characteristics being indicative of a simultaneous change of emotional state of the first person and the second person; and in response to determining that the set of one or more features matches the set of one or more predetermined characteristics, transmit a trigger signal to the capturing device.

This aspect may generally present the same or corresponding features as the former aspect wherein reference is made to the above discussion.

The apparatus may thus provide a data processing scheme, for example, in the form of an algorithm, for determining whether a condition for emotion-triggered capture of audio and/or image data prevails. The apparatus may make use, or be connected to, an audio and/or image capturing device, which may be pre-installed to capture audio and/or images from a scene. The apparatus may further make use of sensors which may provide information about the emotional state of persons and which are already being used by the first and the second person, such as in the form of wearable sensors, which may, for example, be connected to a smart phone.

With the apparatus, an emotion-triggered control of capture of audio and/or image data may be implemented in a scene, wherein an audio and/or image data capturing device is available and wherein physiological data and voice audio data is already being captured.

In a third aspect, the present disclosure relates to a system for emotion-triggered capturing of audio and/or image data. The system comprises: an apparatus according to the second aspect of the disclosure, a first sensor adapted to acquire first physiological data representing a first physiological parameter corresponding to a first person, a second sensor adapted to acquire second physiological data representing a second physiological parameter corresponding to a second person, and an audio sensor adapted to acquire voice audio data.

This aspect may generally present the same or corresponding features as the former aspects wherein reference is made to the above discussion.

According to this aspect of the disclosure, the system includes sensors for acquiring data allowing determination of the simultaneous change of emotional state of the first and the second person.

According to an example embodiment, the audio sensor comprises a first audio sensor and a second audio sensor. The first and the second audio sensor may be arranged to separately detect voice audio data from the first person and the second person. For instance, a first and a second audio sensor may be used in a videoconferencing application, wherein the first person and the second person are not in the same physical location.

According to an example embodiment, the system further comprises: a capturing device adapted to capture audio and/or image data. Thus, the processing unit may be arranged to transmit or output a trigger signal to a capturing device that is part of the system.

According to an example embodiment, the system further comprises: a capturing device including at least one of video camera, a still image camera and a microphone adapted to capture audio and/or image data. Thus, the processing unit may be arranged to transmit a trigger signal to a capturing device that is part of the system. In some example embodiments, a plurality of capturing devices may be included in the system in order to capture a plurality of recordings of an event, such as both video and audio recordings.

According to an example embodiment, the system further comprises a storage unit adapted to store the captured audio and/or image data. Thus, the captured audio and/or image data may be stored in the system in order to allow later access of audio and/or image data, for example, for transfer to an external unit or for playback of the audio and/or image data.

It is noted that the disclosure relates to all possible combinations of features recited in the claims.

BRIEF DESCRIPTION OF THE FIGURES

The above, as well as additional, features will be better understood through the following illustrative and non-limiting detailed description of example embodiments, with reference to the appended drawings.

This and other aspects of the present disclosure will now be described in more detail, with reference to the appended drawings showing embodiments of the disclosure. Like reference numerals refer to like elements throughout.

All the figures are schematic, not necessarily to scale, and generally only show parts which are necessary to elucidate example embodiments, wherein other parts may be omitted or merely suggested.

DETAILED DESCRIPTION

Example embodiments will now be described more fully hereinafter with reference to the accompanying drawings. That which is encompassed by the claims may, however, be embodied in many different forms and should not be construed as limited to the embodiments set forth herein; rather, these embodiments are provided by way of example, and for thoroughness and completeness, and fully convey the scope of the disclosure to the skilled person. Furthermore, like numbers refer to the same or similar elements or components throughout.

Figure 1:
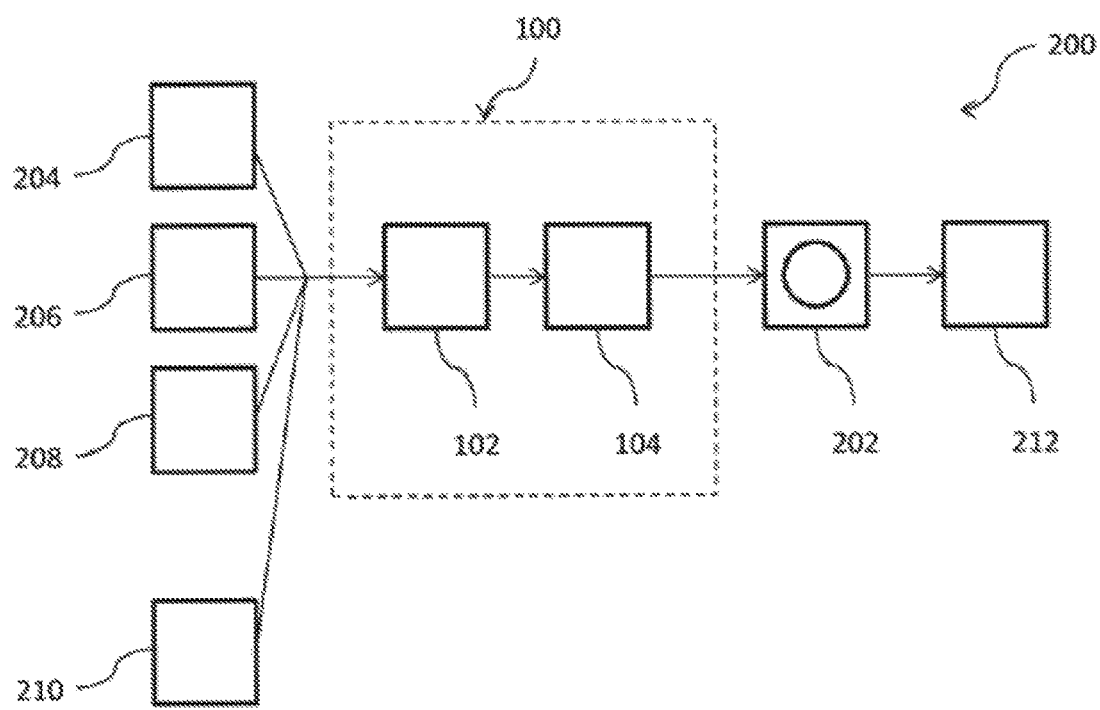
FIG. 1 is a schematic view of a system comprising an apparatus according to an example embodiment.

Referring to the figures and in particular to FIG. 1 here is conceptually depicted an apparatus 100 for emotion-triggered control of capture of audio and/or image data by an audio and/or image capturing device 202. The apparatus 100 may be arranged within a system 200 which will be described in more detail below.

The apparatus 100 will first be described. The apparatus 100 comprises data input circuitry 102. The data input circuitry 102 is adapted to receive a time-sequential set of data. More specifically, the time-sequential set of data includes a first physiological data representing a first physiological parameter corresponding to a first person 302, a second physiological data representing a second physiological parameter corresponding to a second person 304, and voice audio data including a voice of at least one of the first 302 and the second 304 person.

The apparatus 100 further comprises a processing unit 104. The processing unit 104 is adapted to analyze the time-sequential set of data. The processing unit 104 is more specifically adapted to analyze the time-sequential set of data to determine whether a set of one or more features obtainable from the set of data matches a set of one or more predetermined characteristics being indicative of a simultaneous change of emotional state of the first person 302 and the second person 304. Further, the processing unit 104 is adapted to in response to determining that the set of one or more features matches the set of one or more predetermined characteristics, generate and transmit or output a trigger signal to the capturing device 202.

The apparatus 100 is able to continuously and automatically analyze the time-sequential set of data to determine a simultaneous change of emotional state of the first person 302 and the second person 304 and to transmit a trigger signal to a capturing device 202.

The apparatus 100 may be implemented in hardware, or as any combination of software and hardware. The apparatus 100 may, for instance, be implemented as software being executed on a general-purpose computer, as firmware arranged, for example, in an embedded system, or as a specifically designed processing unit, such as an Application-Specific Integrated Circuit (ASIC) or a Field-Programmable Gate Array (FPGA).

The time-sequential set of data may be received by the data input circuitry 102 of the apparatus 100 in various forms and through various types of communication channels. For instance, the time-sequential set of data may be received by the data input circuitry 102 through a wired connection using electrical wirings or optical fibers. Moreover, the time-sequential set of data may be received by the data input circuitry 102 through a wireless connection, such a Wi-Fi, Bluetooth, ZigBee connection or similar. The input circuitry 102 may for that reason comprise circuitry adapted to receive the time-sequential set of data in a particular format, or to receive the time-sequential set of data in a plurality of suitable formats. The time-sequential set of data may thus in other words be received through a galvanic connection or a non-galvanic connection.

In the following the system 200 of FIG. 1 will be described in more detail. The depicted system 200 comprises an apparatus 100 as described above. The system 200 further comprises a first sensor 204 adapted to acquire first physiological data representing a first physiological parameter corresponding to a first person 302 and a second sensor 206 adapted to acquire second physiological data representing a second physiological parameter corresponding to a second person 304.

Moreover, the depicted system 200 comprises an audio sensor 208 adapted to acquire voice audio data.

The first sensor 204 and the second sensor 206 may be of the same type or of different types. The first sensor 204 and the second sensor 206 may be arranged on the persons 302, 304, from whom the first physiological data and the second physiological data are to be acquired, or the first sensor 204 and the second sensor 206 may be arranged in proximity to the persons 302, 304. In other words, the first sensor 204 and the second sensor 206 may be worn by the persons 302, 304, from whom the first physiological data and the second physiological data are to be acquired or may be arranged without any physical contact with the persons 302, 304. Moreover, sensors already used by the persons, such as sensors arranged in or connected to a smart phone or a smart watch may be used.

The first sensor 204 and the second sensor 206 may be any kind of sensors which are capable of acquiring physiological data from a person 302, 304. The sensors 204, 206 may be, but not limited to, a galvanic skin response sensor, an electroencephalogram sensor, a photoplethysmogram sensor, a bio-impedance sensor, an electromyogram sensor, an electrooculogram sensor and an electrocardiogram sensor. Each of the sensors 204, 206 may further be capable of acquiring physiological data representing one of more physiological parameters. It is thus to be understood that the wording sensor is to be interpret in its broadest sense where each of the sensors 204, 206 may be a complex assembly suitable for determining one or more physiological parameter of a person 302, 304. Moreover, the sensors 204, 206 may include processing capabilities for processing the acquired data to output data in a desired format, such as a standard format or a customized format.

It is to be noted that more than two sensors 204, 206 for acquiring physiological data representing a physiological parameter may be used in the system 200. For instance, the system 200 may be used in a concert hall with hundreds of people. In this particular case, hundreds of sensors 204, 206 for acquiring physiological data representing a physiological parameter may be used in the system 200. In fact any person present in the concert hall may for instance wear a sensor for acquiring physiological data representing a physiological parameter. On the other hand, a selected number of the persons may for instance wear a sensor for acquiring physiological data representing a physiological parameter. In other words, the system 200 may be used on a large number of persons and is by no means limited to be used with only a couple of persons 204, 206.

The audio sensor 208 may be a microphone or any other suitable type of sensor capable of acquiring voice audio data. The audio sensor 208 may be arranged in any suitable location where voices of the persons 204, 206 are audible such that voice audio data may be acquired. The sensor 208 may for example be located on one of the persons, within a room 300 or confined space where the persons are located. Further, the audio sensor 208 may be integral to the capturing device 202, such as a microphone present in a surveillance camera. Another example is to use a microphone present in a handheld device such as a smart phone or similar.

Moreover, the audio sensor 208 may include processing capabilities for processing the acquired data to output data in a desired format, such as a standard format or a customized format.

The first sensor 204, the second sensor 206 and the audio sensor 208 may be connected to the apparatus 100 using any suitable connection, wired or wireless.

In addition to the first audio sensor 208, the system may comprise a second audio sensor 210. The first audio sensor 208 and the second audio sensor 210 may be thus be arranged in separate locations to detect and acquire voice audio data of persons who are not located in at the same location. For instance, a first audio sensor 208 and a second audio sensor 210 may be used in a videoconferencing application, wherein the first person 204 and the second person 206 are not in the same physical location. Moreover, the use of a first audio sensor 208 and a second audio sensor 210 may bring advantages in noisy environments, where ambient sounds could increase the risk of disturbance. Further, it is to be understood that any number of audio sensors 208, 210 may be used depending on the needs.

In addition to the above, the system 200 may comprise a capturing device 202 adapted to capture audio and/or image data. The capturing device 202 may include a still camera or a video camera for capturing still and motion pictures respectively. Moreover, the capturing device 202 may include a microphone or any other suitable device capable of capturing audio data. The capturing device 202 may thus be capable of capturing image and audio data. This may for instance be realized by combining a camera of some type with a microphone or similar. Still images and/or motion images may be combined with audio data. In other words, images and audio may be captured and combined into common data as is known in the art.

In addition to the above, the system 200 may comprise a storage unit 212 adapted to store the captured audio and/or image data. By including a storage unit 212 in the system 200, the captured audio and/or image data may be stored in order to allow later access. By this arrangement, the captured audio and/or image data may be transferred elsewhere or played when desired. The storage unit 212 may be any type of storage unit capable of storing audio and/or image data as acquired by the capturing device 202. Non-limiting examples of suitable devices are a hard drive, a flash memory, an optical storage media or similar.

Moreover, the storage device 212 may include processing capabilities for compressing the stored data in order to save space. The storage device 212 may be connected to the capturing device 202 using any suitable connection, wired or wireless.

Figure 2:
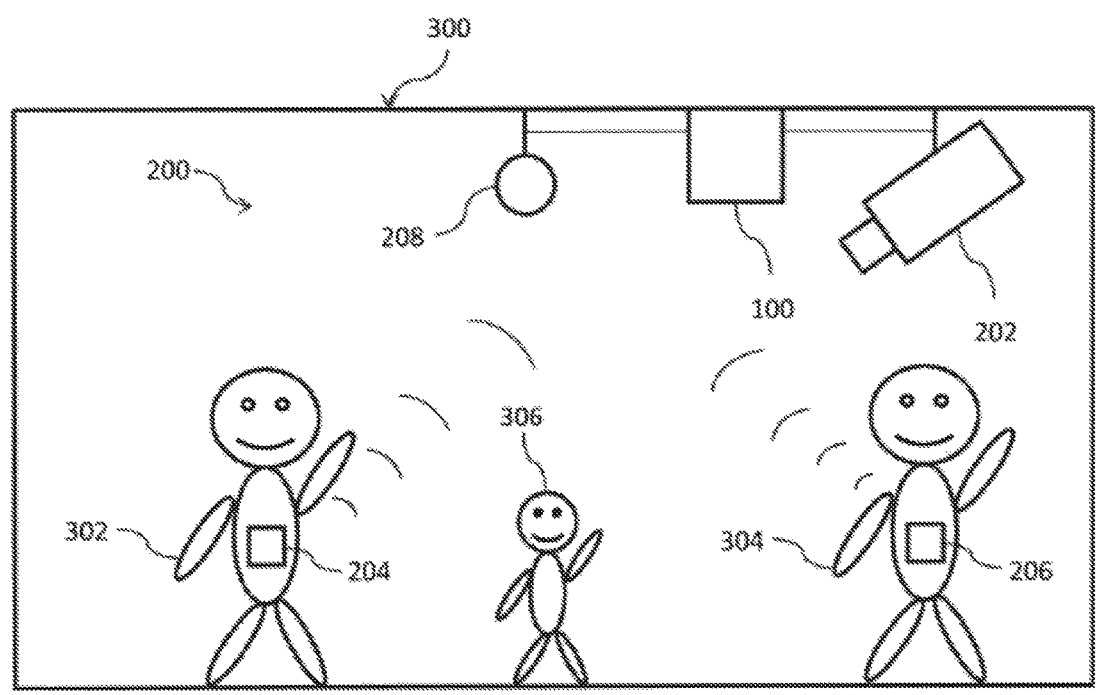
FIG. 2 is a schematic view of a room comprising a system according to an example embodiment.

Now referring particularly to FIG. 2, here is conceptually depicted how the system 200 of FIG. 1 may be used to capture audio and image data in a particular situation where a baby 306 takes its first steps in a home environment in form of room 300. The use of the system 200 is below exemplified in a situation where physiological data representing a physiological parameter is acquired from two persons 302, 304 only, for reasons of simplicity. However, as described above, the system 200 may be used in a situation where a large number of persons are involved and where data representing a physiological parameter form a large number of persons 302, 304 are acquired using a large number of sensors 204, 206, 208, 210.

In FIG. 2 a baby 306, his mother 302 (a first person) and his father 304 (a second person) are present in a room 300. The room 300 is employed with an apparatus 100 of the above described kind. The room 300 is further employed with an audio sensor 208 in form of a microphone. Further, a capturing device 202 in form of a surveillance camera is installed in the room 300. The surveillance camera is capable of capturing motion pictures and audio. In other words, the room 300 is employed with a system 200 of the above described kind.

The mother 302 wears a first sensor 204 adapted to acquire first physiological data representing a first physiological parameter. Similarly, the father 304 wears a second sensor 206 adapted to acquire second physiological data representing a second physiological parameter. The audio sensor 208 is adapted to acquire voice audio data from the room 300, i.e., voice audio data from the mother 302, the father 304 and the baby 306. The first sensor 204 and the second sensor 206 are connected to the apparatus 100 by means of a wireless Wi-Fi connection. The audio sensor 208 and the capturing device 202 are connected to the apparatus 100 by means of a wired connection.

When the system 200 is in use, the apparatus 100, the first sensor 204, the second sensor 206 and the audio sensor 208 are all activated. The first sensor 204, the second sensor 206 and the audio sensor 208 thereby acquire their respective data and feed the data to the apparatus 100, thereby producing a time-sequential set of data including first physiological data representing a first physiological parameter corresponding to the mother 302, a second physiological data representing a second physiological parameter corresponding to the father 304, and voice audio data including a voice of at least one of the mother 302 and the father 304, depending on who is talking at the moment. The time-sequential set of data so produced is fed to the data input circuitry 102 of the apparatus 100 as described above.

The time-sequential set of data is then analyzed by the processing unit 104 of the device 100. More specifically, the time-sequential set of data is analyzed by the processing unit 104 to determine whether a set of one or more features obtainable from the set of data matches a set of one or more predetermined characteristics, where the characteristics are being indicative of a simultaneous change of emotional state of the mother 302 and the father 304. In the present example, the mother 302 and the father 304 becomes very happy at the same instant when their baby 306 takes its first steps. In other words, the mother 302 and the father 304 experience a simultaneous change of emotional state which will be determined by the processing unit 104 of the apparatus 100.

It is to be noted that the set of one or more features obtainable from the set of data may be analyzed individually or in combination to determine if the set of data matches a set of one or more predetermined characteristics being indicative of a simultaneous change of emotional state. In other words, it may also be determined whether a set of features based on the first physiological data, the second physiological data and the voice audio data in combination corresponds to a set of characteristics indicative of a change of emotional state.

The processing unit 104 then generates and transmits a trigger signal to the capturing device 202 as a response to determining that the set of one or more features matches the set of one or more predetermined characteristics, i.e., in response to determining that the mother 302 and the father 304 experience a simultaneous change of emotional state. The trigger signal so produced activates the capturing device 202 which captures the moment, by recording motion pictures and audio of the baby 306 taking its first steps. The recorded motion pictures and audio are stored in a storage unit 212, connected to the capturing device 202, for later access.

In the above example, a change of emotional state of the mother 302 may occur at a first point of time and a change of emotional state of the father 304 may occur at a second point of time although originating from the same event, for example, when the baby 306 takes its first steps. In other words, the mother 302 may react by being very happy slightly faster than the father 304 or vice versa. It may thus be important to determine whether a simultaneous change of emotional state of the mother 302 and the father 304 occurred based on the difference between the first and second points of time in order to transmit a trigger signal to the capturing device 202 when relevant. This in order to not miss the moment when the baby 306 takes its first steps.

In the following, the acquiring of physiological data and voice audio data will be described and exemplified. A plurality of non-limiting examples will be given on how the data may be acquired, represented and analyzed. The skilled person realizes that other ways of acquiring, representing and analyzing may be employed without departing from the scope of the present concept.

To be able to produce physiological data representing a physiological parameter corresponding to a person 302, 304, measurements pertaining to the physiological parameter corresponding to the person in question will have to be carried out. For that reason several known techniques for measuring physiological parameters on a person 302, 304 may be employed. For instance, the following techniques may be used; galvanic skin response, electroencephalogram, photoplethysmogram, bio-impedance, electromyogram, electrooculogram and electrocardiogram. It is consequently possible to make use of a plurality of techniques to measure physiological parameters on the person in question to acquire data. The so acquired data may be used directly, i.e., as is, or may be subject to data processing where information is extracted from the data.

The directly acquired data or the extracted information may be included in a set of one or more features and analyzed to determine whether the set of one or more features matches a set of one or more predetermined characteristics being indicative of a simultaneous change of emotional state. Examples of such features which are pertaining directly or indirectly to measurements of physiological parameters are: a skin electrical resistance, a variation of a skin electrical resistance, an increase of a skin electrical resistance, a decrease of a skin electrical resistance, a skin electrical conductance, a variation of a skin electrical conductance, an increase of a skin electrical conductance, a decrease of a skin electrical conductance, a skin electrical potential, a variation of a skin electrical potential, an increase of skin electrical potential, a decrease of a skin electrical potential, a skin electrical impedance, a variation of a skin electrical impedance, an increase of a skin electrical impedance, a decrease of a skin electrical impedance, a skin conductance response rate, a variation of a skin conductance response rate, an increase of a skin conductance response rate, a decrease of a skin conductance response rate, a skin ohmic perturbation duration, a variation of a skin ohmic perturbation duration, a brain volume conduction, a variation of a brain volume conduction, an increase of a brain volume conduction, a decrease of a brain volume conduction, a brain channel frequency band power, a variation of a brain channel frequency band power, a brain channel correlation, a variation of a brain channel correlation, a brain frequency band coherence, a variation of a brain frequency band coherence, a brain frequency asymmetry, a variation of a brain frequency asymmetry, an electrical heart signal, a variation of an electrical heart signal, an increase of an electrical heart signal, a decrease of an electrical heart signal, a heart rate, a variation of a heart rate, an increase of a heart rate, a decrease of a heart rate, a standard deviation of a heart N-N interval, a variation of a standard deviation of a heart N-N interval, a heart rate variability, a variation of a heart rate variability, an electrical potential generated by muscle cells, a variation of such electrical potential, an increase of such electrical potential, a decrease of such electrical potential, a corneo-retinal standing potential as a measurement of an eye position, a variation of corneo-retinal standing potential, an increase of corneo-retinal standing potential, and a decrease of corneo-retinal standing potential.

Moreover, features pertaining to the physiological parameters may be determined by analysis of the time-sequential behavior of the physiological data acquired from the persons 302, 304 who are subject to measurement of physiological data representing a physiological parameter. Hence, in case physiological data representing physiological parameters are acquired from two persons 302, 304, features may be determined by analysis of the respective parameters, i.e., the first physiological parameter and the second physiological parameter. The features may then for instance include; a variation of the first physiological parameter, a variation of the second physiological parameter, a maximum value of the first physiological parameter, a maximum value of second physiological parameter, a mean value of the first physiological parameter, a mean value of the second physiological parameter, a standard deviation of the first physiological parameter, a standard deviation of the second physiological parameter, a correlation of the first physiological parameter, a correlation of the second physiological parameter, a coherence of the first physiological parameter, a coherence of the second physiological parameter, an increase of the first physiological parameter, an increase of the second physiological parameter, a decrease of the first physiological parameter, a decrease of the second physiological parameter, a cease of the first physiological parameter, and a cease of the second physiological parameter.

The set of one or more features may comprise low-level features, which may be directly extracted from the time-sequential set of data. However, the set of one or more features may also comprise high-level concepts, which may be derived by applying data analysis on the time-sequential set of data. Thus, the time-sequential set of data may first be analyzed to determine features corresponding to high-level concepts by means of applying data analysis on the time-sequential set of data. Then, the high-level concepts may be used as features, possibly together with low-level features, which are matched to a set of predetermined characteristics.

Similarly, features may be extracted directly or indirectly from the voice audio data acquired by the audio sensor 208, or any additional audio sensor 210. Examples of such features which are pertaining directly or indirectly to the voice audio data acquired by the audio sensor 208 are: an amplitude of the voice audio data, a variation of an amplitude of the voice audio data, an increase of an amplitude of the voice audio data, a decrease of an amplitude of the voice audio data, a pitch of the voice audio data, a variation of a pitch of the voice audio data, mel-frequency spectral coefficients of the voice audio data, a variation of mel-frequency spectral coefficients of the voice audio data, linear prediction spectral coefficients of the voice audio data, a variation of linear prediction spectral coefficients of the voice audio data, a time separation between consecutive sounds of the voice audio data, a variation of a time separation between consecutive sounds of the voice audio data, an increase of a time separation between consecutive sounds of the voice audio data, a decrease of a time separation between consecutive sounds of the voice audio data, a background noise level of the voice audio data, a variation of a background noise level of the voice audio data, an increase of a background noise level of the voice audio data, a decrease of a background noise level of the voice audio data, a predominant frequency of the voice audio data, a variation of a predominant frequency of the voice audio data, an increase of a predominant frequency of the voice audio data and a decrease of a predominant frequency of the voice audio data. It is thus to be understood that the influence of the more complex concepts like the words spoken, the voice level, the voice intensity, laughter, yelling, etc. may be taken into account by the above exemplified features.

In analyzing the above described time-sequential set of data as received by the data input circuitry 102 of the apparatus 100, several strategies may be employed by the processing unit 104. As discussed above, the analysis may be performed in order to determine whether a set of one or more features obtainable from the set of data matches a set of one or more predetermined characteristics being indicative of a simultaneous change of emotional state of the persons involved. Also as discussed above, the features may be represented in numerous ways. Also the predetermined characteristics which are indicative of a simultaneous change of emotional state of the persons involved may be represented in different ways and may also be determined in different ways. It is thus to be understood that it is reasonable to choose a limited number of features to be considered and matched in a particular case. The features chosen in a particular case may depend on several things, such as the sensors 204, 206, 208, 210 available, the number of persons 302, 304 involved, the environment in which the system 200 is used, etc. The choice of features to be considered in a particular case may thus be automatically determined by the system 200 based on, for example, the hardware available or may be specified by a user setting up the system 200.

The predetermined characteristics which are to be considered and matched with a particular set of features may for instance be represented as numbers in a database, where each number is represented by a numerical value linked to a particular feature. The matching of the set of features with the predetermined characteristics being indicative of a simultaneous change of emotional state may be performed in a number of ways. For example, classification using certain rules may be employed. The rules may as an example specify how the set of features in question are to change over time in order to be considered to match the predetermined characteristics in question.

Further, the matching of a particular set of features with predetermined characteristics may for instance include determining whether one or more of the features exceeds a predetermined set of thresholds or determining whether one or more of the features fall below a predetermined set of thresholds.

Also more sophisticated machine learning techniques may be employed in matching a set of features with predetermined characteristics. In this case the machine learning may start from a preprogrammed database but may be improved over time by updating the database or by being provided by user feedback.

The matching aiming at determining a simultaneous change of emotional state of the persons involved may further make use of one or more classifiers or relevance estimation methods such as k-nearest neighbors (KNN), Hidden Markov Model (HMM), Support Vector Machine (SVM), Artificial Neural Network (ANN), and Gaussian Mixtures Model (GMM).

The set of one or more predetermined characteristics may moreover include group profiles, which define a combination of a plurality of predetermined characteristics in relation to the persons 302, 304 involved. In this case the plurality of predetermined characteristics is correlated with respect to a simultaneous change of emotional state of the first person 302 and the second person 304. With this approach it is thus possible to match a set of features for a person 302 in parallel with a set of features for another person 304 with the characteristics of the group profile in question. It is thus possible, in parallel for a plurality of persons, to determine whether a change of emotional state occurs and if the changes so determined are simultaneous.

In an embodiment, the time-sequential set of data may be analyzed to generate a set of features, which may comprise several sub-sets of features. Such sub-sets may for instance include one or more of: low-level audio-based features, high-level audio-based concepts, low-level galvanic skin response based features, high-level galvanic skin response based concepts, low-level electrocardiogram-based features, high-level electrocardiogram-based concepts, low-level electroencephalogram-based features, and high-level electroencephalogram-based concepts. Each sub-set may comprise features for a plurality of persons 302, 304.

The processing unit 104 may further include or have access to a database storing a set of predetermined characteristics in the form of personalized profiles indicating characteristics of a specific person corresponding to a change of emotional state, and a set of predetermined characteristics in the form of group profiles.

The processing unit 104 may be arranged to perform a plurality of analyses based on the low-level features and high-level concepts. The processing unit 104 may thus be arranged to analyze an emotional predominance in a scene as a whole, based on low-level features of a plurality of persons 302, 304. The processing unit 104 may further be arranged to analyze an emotional predominance in a scene as a whole, based on high-level concepts of a plurality of persons 302, 304. The processing unit 104 may further be arranged to separately analyze an emotional state of each person 302, 304, based on low-level features of the respective persons 302, 304. The processing unit 104 may further be arranged to separately analyze an emotional state of each person 302, 304, based on high-level concepts of the respective persons 302, 304. Based on such plurality of analyses, the processing unit 104 may further make a determination whether a simultaneous change of emotional state has occurred in the scene.

Figure 3:
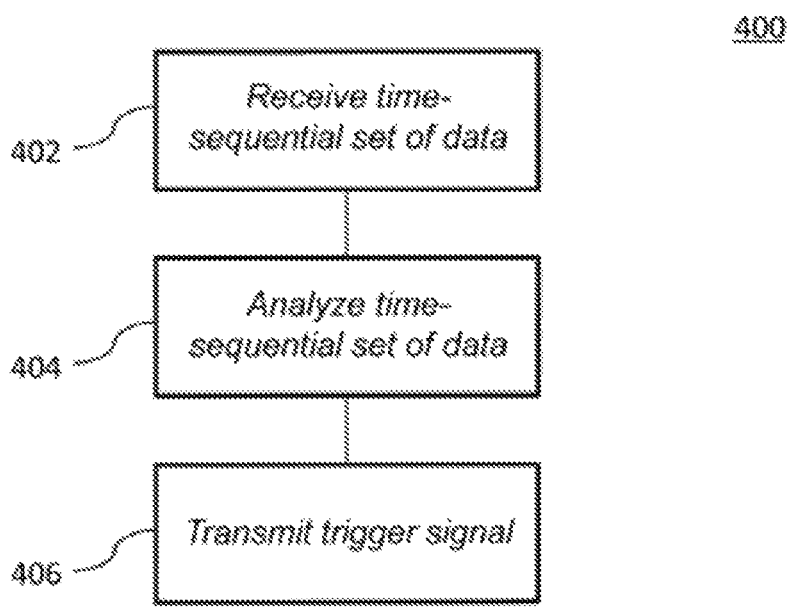
FIG. 3 is a flow chart of a method according to an example embodiment.

Referring now to FIG. 3, a method 400 for emotion-triggered capturing of audio and/or image data by an audio and/or image capturing device will be generally described.

The method comprises receiving, step 402, a time-sequential set of data including first physiological data representing a first physiological parameter corresponding to a first person 302, a second physiological data representing a second physiological parameter corresponding to a second person 304, and voice audio data including a voice of at least one of the first 302 and the second 304 person.

The received time-sequential set of data is analyzed, step 404, to determine whether a set of one or more features obtainable from the set of data matches a set of one or more predetermined characteristics being indicative of a simultaneous change of emotional state of the first person 302 and the second person 304.

In response to determining that the set of one or more features matches the set of one or more predetermined characteristics, a trigger signal may be transmitted, step 406, to the capturing device 202.

In the above the disclosure has mainly been described with reference to a limited number of embodiments. However, as is readily appreciated by a person skilled in the art, other embodiments than the ones disclosed above are equally possible within the scope of the disclosure, as defined by the appended claims.

Additionally, variations to the disclosed embodiments can be understood and effected by the skilled person in practicing the claimed disclosure, from a study of the drawings, the disclosure, and the appended claims. In the claims, the word "comprising" does not exclude other elements or steps, and the indefinite article "a" or "an" does not exclude a plurality. The mere fact that certain measures are recited in mutually different dependent claims does not indicate that a combination of these measured cannot be used to advantage.

While some embodiments have been illustrated and described in detail in the appended drawings and the foregoing description, such illustration and description are to be considered illustrative and not restrictive. Other variations to the disclosed embodiments can be understood and effected in practicing the claims, from a study of the drawings, the disclosure, and the appended claims. The mere fact that certain measures or features are recited in mutually different dependent claims does not indicate that a combination of these measures or features cannot be used. Any reference signs in the claims should not be construed as limiting the scope.

What is claimed is:

1. A method for emotion-triggered capturing of audio or image data by an audio or image capturing device, the method comprising:
   receiving a time-sequential set of data including first physiological data representing a first physiological parameter corresponding to a first person, second physiological data representing a second physiological parameter corresponding to a second person, and voice audio data including a voice of at least one of the first person and the second person;
   analyzing the time-sequential set of data to determine whether a set of one or more features obtainable from the time-sequential set of data matches a set of one or more predetermined characteristics being indicative of respective changes of emotional state of the first person and emotional state of the second person being less than a threshold time difference; and
   in response to determining that the set of one or more features matches the set of one or more predetermined characteristics, transmitting a trigger signal to the audio or image capturing device.

2. The method according to claim 1, wherein the analyzing comprises:
   determining whether a set of features based on the first physiological data, the second physiological data, and the voice audio data in combination corresponds to a set of characteristics indicative of a change of emotional state of both the first person and the second person.

3. The method according to claim 1, wherein the analyzing comprises:
   identifying that the first physiological data and the voice audio data represents a first change of emotional state of the first person at a first point of time in the time-sequential set of data;
   identifying that the second physiological data and the voice audio data represents a second change of emotional state of the second person at a second point of time in the time-sequential set of data; and
   determining whether a simultaneous change of emotional state of the first person and emotional state of the second person occurred based on a difference between the first point of time and the second point of time.

4. The method according to claim 1, wherein the set of one or more features comprises low-level features, which may be directly extracted from the time-sequential set of data, and high-level concepts, which may be derived by applying data analysis on the time-sequential set of data.

5. The method according to claim 1, wherein the set of one or more predetermined characteristics includes group profiles, which define a combination of a plurality of predetermined characteristics in relation to the first person and the second person, which plurality of predetermined characteristics are correlated with respect to respective changes of emotional state of the first person and emotional state of the second person being less than a threshold time difference.

6. The method according to claim 1, wherein the set of one or more features includes one or more of: a variation of the first physiological parameter, a variation of the second physiological parameter, a maximum value of the first physiological parameter, a maximum value of the second physiological parameter, a mean value of the first physiological parameter, a mean value of the second physiological parameter, a standard deviation of the first physiological parameter, a standard deviation of the second physiological parameter, a correlation of the first physiological parameter, a correlation of the second physiological parameter, a coherence of the first physiological parameter, a coherence of the second physiological parameter, an increase of the first physiological parameter, an increase of the second physiological parameter, a decrease of the first physiological parameter, a decrease of the second physiological parameter, a cease of the first physiological parameter, and a cease of the second physiological parameter.

7. The method according to claim 1, wherein the set of one or more features includes one or more of: an amplitude of the voice audio data, a variation of an amplitude of the voice audio data, an increase of an amplitude of the voice audio data, a decrease of an amplitude of the voice audio data, a pitch of the voice audio data, a variation of a pitch of the voice audio data, mel-frequency spectral coefficients of the voice audio data, a variation of mel-frequency spectral coefficients of the voice audio data, linear prediction spectral coefficients of the voice audio data, a variation of linear prediction spectral coefficients of the voice audio data, a time separation between consecutive sounds of the voice audio data, a variation of a time separation between consecutive sounds of the voice audio data, an increase of a time separation between consecutive sounds of the voice audio data, a decrease of a time separation between consecutive sounds of the voice audio data, a background noise level of the voice audio data, a variation of a background noise level of the voice audio data, an increase of a background noise level of the voice audio data, a decrease of a background noise level of the voice audio data, a predominant frequency of the voice audio data, a variation of a predominant frequency of the voice audio data, an increase of a predominant frequency of the voice audio data, and a decrease of a predominant frequency of the voice audio data.

8. The method according to claim 1, wherein the first physiological parameter and the second physiological parameter include one or more of: galvanic skin response, electroencephalogram, photoplethysmogram, bio-impedance, electromyogram, electrooculogram and electrocardiogram.

9. The method according to claim 8, wherein the set of one or more features includes one or more of: information extractable from galvanic skin response, electroencephalogram, photoplethysmogram, bio-impedance, electromyogram, electrooculogram or electrocardiogram measurements.

10. The method according to claim 1, wherein the determining of whether the set of one or more features obtainable from the time-sequential set of data matches a set of one or more predetermined characteristics includes one or more of: determining whether one or more of the set of one or more features exceeds a predetermined set of thresholds, determining whether one or more of the set of one or more features fall below a predetermined set of thresholds, and determining whether one or more of the set of one or more features corresponds to a predetermined set of characteristics.

11. An apparatus for emotion-triggered control of capture of audio or image data by an audio or image capturing device, the apparatus comprising:
  data input circuitry adapted to:
    receive a time-sequential set of data including first physiological data representing a first physiological parameter corresponding to a first person, second physiological data representing a second physiological parameter corresponding to a second person, and voice audio data including a voice of at least one of the first and the second person, and
  a processing unit adapted to:
    analyze the time-sequential set of data to determine whether a set of one or more features obtainable from the time-sequential set of data matches a set of one or more predetermined characteristics being indicative of respective changes of emotional state of the first person and emotional state of the second person being less than a threshold time difference; and
    in response to determining that the set of one or more features matches the set of one or more predetermined characteristics, transmit a trigger signal to the audio or image capturing device.

12. A system for emotion-triggered capturing of audio or image data, the system comprising:
  an apparatus according to claim 11;
  a first sensor adapted to acquire first physiological data representing a first physiological parameter corresponding to a first person;
  a second sensor adapted to acquire second physiological data representing a second physiological parameter corresponding to a second person; and
  an audio sensor adapted to acquire voice audio data.

13. The system according to claim 12, wherein the audio sensor comprises a first audio sensor and a second audio sensor.

14. The system according to claim 12, the system further comprising:
  a capturing device including at least one of video camera, a still image camera, and a microphone adapted to capture audio or image data.

15. The system according to claim 14, the system further comprising a storage unit adapted to store the captured audio or image data.

16. The system according to claim 12, wherein the set of one or more features comprises low-level features, which may be directly extracted from the time-sequential set of data, and high-level concepts, which may be derived by applying data analysis on the time-sequential set of data.

17. The system according to claim 12, wherein the set of one or more predetermined characteristics includes group profiles, which define a combination of a plurality of predetermined characteristics in relation to the first person and the second person, which plurality of predetermined characteristics are correlated with respect to respective changes of emotional state of the first person and emotional state of the second person being less than a threshold time difference.

18. The system according to claim 12, wherein the set of one or more features includes one or more of: a variation of the first physiological parameter, a variation of the second physiological parameter, a maximum value of the first physiological parameter, a maximum value of second physiological parameter, a mean value of the first physiological parameter, a mean value of the second physiological parameter, a standard deviation of the first physiological parameter, a standard deviation of the second physiological parameter, a correlation of the first physiological parameter, a correlation of the second physiological parameter, a coherence of the first physiological parameter, a coherence of the second physiological parameter, an increase of the first physiological parameter, an increase of the second physiological parameter, a decrease of the first physiological parameter, a decrease of the second physiological parameter, a cease of the first physiological parameter, and a cease of the second physiological parameter.

19. The system according to claim 12, wherein the set of one or more features includes one or more of: an amplitude of the voice audio data, a variation of an amplitude of the voice audio data, an increase of an amplitude of the voice audio data, a decrease of an amplitude of the voice audio data, a pitch of the voice audio data, a variation of a pitch of the voice audio data, mel-frequency spectral coefficients of the voice audio data, a variation of mel-frequency spectral coefficients of the voice audio data, linear prediction spectral coefficients of the voice audio data, a variation of linear prediction spectral coefficients of the voice audio data, a time separation between consecutive sounds of the voice audio data, a variation of a time separation between consecutive sounds of the voice audio data, an increase of a time separation between consecutive sounds of the voice audio data, a decrease of a time separation between consecutive sounds of the voice audio data, a background noise level of the voice audio data, a variation of a background noise level of the voice audio data, an increase of a background noise level of the voice audio data, a decrease of a background noise level of the voice audio data, a predominant frequency of the voice audio data, a variation of a predominant frequency of the voice audio data, an increase of a predominant frequency of the voice audio data, and a decrease of a predominant frequency of the voice audio data.

20. The system according to claim 12, wherein the first physiological parameter and the second physiological parameter include one or more of: galvanic skin response, electroencephalogram, photoplethysmogram, bio-impedance, electromyogram, electrooculogram and electrocardiogram.

* * * * *